United States Patent [19]

Fitzig et al.

[11] Patent Number: 4,699,423

[45] Date of Patent: Oct. 13, 1987

[54] CHAIR SYSTEM PARTICULARLY USEFUL FOR A DENTAL OFFICE

[75] Inventors: Simon Fitzig, Tel-Aviv; Barry Marshak, Ramat Poleg, both of Israel

[73] Assignee: Ramot University Authority for Applied Research & Industrial Development Ltd., Tel Aviv, Israel

[21] Appl. No.: 7,288

[22] Filed: Jan. 27, 1987

[30] Foreign Application Priority Data

Jan. 28, 1986 [IL] Israel ............................... 77730

[51] Int. Cl.$^4$ ............................................. A47C 15/00
[52] U.S. Cl. ...................................... 297/245; 297/195; 297/240; 297/257; 297/392
[58] Field of Search ............... 297/245, 241, 242, 240, 297/195, 392, 487, 488, 232, 257

[56] References Cited

U.S. PATENT DOCUMENTS

| | | | |
|---|---|---|---|
| 336,220 | 2/1886 | Farrar | 297/242 |
| 1,731,709 | 10/1929 | Cropsey | 297/392 X |
| 2,542,653 | 2/1951 | Frydenlund | 297/242 |
| 2,602,485 | 7/1952 | Alloway | 297/240 |
| 4,607,882 | 8/1986 | Opsvik | 297/195 |
| 4,650,249 | 3/1987 | Serber | 297/195 X |

Primary Examiner—Francis K. Zugel
Attorney, Agent, or Firm—Benjamin J. Barish

[57] ABSTRACT

A chair system particularly useful for a dental office or other operatory wherein the head region of a subject is to be treated by a dentist or other operator, comprises a subject's chair for seating the subject in an upright position; an operator's chair for seating the operator in an upright position facing the subject; and a mounting for mounting the operator's chair at a higher elevation than the subject's chair such that the legs of the operator straddle the legs of the subject when both are seated in their respective chairs. The chair system further includes a vertically-extending barrier between the operator's chair and the subject's chair terminating below the head region of the subject when seated in the subject's chair, separating the operator from the subject but permitting free access by the operator over the top of the barrier to the head region of the subject.

20 Claims, 5 Drawing Figures

CHAIR SYSTEM PARTICULARLY USEFUL FOR A DENTAL OFFICE

BACKGROUND OF THE INVENTION

The present invention relates to a chair system particularly useful for a dental office, but also useful in another type operatory, such as an ophthalmologist's office, wherein the head region of a subject is to be treated by an operator. Since the invention is especially useful for a dental office, it is described below with respect to this application.

At the present time, there are two basic working systems for the treatment of dental patients. In one system, the patient is placed in a sitting or semi-reclining position; and in a second system, the patient is placed in a fully reclining (or almost fully reclining) position. The services of a dental assistant may be used in both systems in order to increase the work efficiency.

In the first system wherein the patient assumes a sitting or a semi-reclining position, the dentist stands at the right hand side or behind the patient. In such a system, the lower jaw is mainly directly viewed by the dentist, but the upper jaw is indirectly viewed (e.g. via mirrors) for both quadrants of the mouth. One main disadvantage of this system is that the standing position of the dentist subjects the dentist to substantial stress and strain, thereby increasing fatigue as well as circulatory problems in the dentist's legs and spinal problems in the dentist's back. Another main disadvantage of this system is the poor visibility of the oral cavity.

In the second system, wherein the patient assumes a full (or almost full) reclining position, the dentist may sit on a stool located at the 9-12 o'clock position on the right hand side of the patient with the dental accessories on the left. This system better enables the use of a dental assistant to provide "four handed dentistry", which allows for better access to the oral cavity and reduces the work time for individual procedures. This system theoretically allows direct vision of all four quadrants of the patient's mouth, or a more comfortable position of the dentist for indirect vision. However, this system also has a number of disadvantages, including the following:

1. The reclining position of the patient produces an accumulation of large amounts of fluid at the back of the patient's throat, which is not only exeedingly uncomfortable for the patient, but also requires the dentist periodically to interrupt the treament in order to permit the patient to rid himself of this fluid.

2. Parallax error is magnified when restoring anterior teeth. This makes it difficult to achieve correct shape and symmetry in the maxillar and mandibular anterior region.

3. Parallelism during tooth preparation is sometimes difficult to judge because of side positioning of the patient's head; i.e. the field of vision of the dentist cannot be perpendicular to the abutment tooth without severe contortioning of the dentist's head.

4. The working position of the dentist places the dentist's upper arms, shoulder, neck and back muscles in tension, resulting in muscle fatigue, muscle ache and stress.

SUMMARY OF THE INVENTION

An object of the present invention is to provide a basic working system for the treatment of dental patients, or other subjects wherein the head region of the subject is to be treated, having advantages in one or more of the above respects.

According to the present invention, there is provided a chair system particularly useful for a dental office or other operatory wherein the head region of a subject is to be treated by a dentist or other operator, comprising: a subject's chair for seating the subject in an upright position; an operator's chair for seating the operator in an upright position facing the subject; a mounting for mounting the operator's chair at a higher elevation than the subject's chair such that the legs of the operator straddle the legs of the subject when both are seated in their respective chairs; and a vertically-extending barrier between the operator's chair and the subject's chair terminating below the head region of the subject when seated in the subject's chair, separating the operator from the subject but permitting free access by the operator over the top of the barrier to the head region of the subject.

Preferably, the barrier includes elbow rests at its upper end for supporting the elbows of the operator when treating the head region of the subject.

In the preferred embodiment of the invention described below, the barrier and the elbow rests are carried by the operator's chair; also, the system further includes foot rests supporting the feet of the operator above the floor, the foot rests being carried by the base of the subject's chair and mounted at an incline to the floor. Further, the subject's chair also includes a chin rest for supporting the chin of the subject during the treatment.

It will be seen that a chair system constructed in accordance with the foregoing features provides a number of important advantages when used for the treatment of dental patients, or other subjects to receive treatment in the head region. Thus, the dentist, or other operator, is seated in the operator's chair so as to be in an upright face-to-face position with respect to the patient (subject), with the legs of the operator straddling the legs of the patient but with the body of the operator separated from the patient by the barrier. The elbow rests at the upper end of the barrier may be used for supporting the elbows of the operator. This places the operator's hands at a work height providing maximum mechanical advantage, with the upper portions of the operator's arms in close proximity to the sides of his body and with the lower portions of his arms extending generally horizontally parallel to the floor. This arrangement thus reduces stress and fatigue on the operator, allows more posibilities of direct vision of the patient's oral cavity at an unstrained position for the operator, reduces parallax errors deviations from parallelism, and is also generally more comfortable to the patient.

Several preferred embodiments of the invention are described below providing for movement of the operator's chair both in the vertical direction and in the horizontal direction to provide for improved access to, and vision of, the subject's oral cavity.

Further features and advantages of the invention will be apparent from the description below.

BRIEF DESCRIPTION OF THE DRAWINGS

The invention is herein described, by way of example only, with reference to the acompanying drawings, wherein.

DESCRIPTION OF A PREFERRED EMBODIMENT

Figure 1:
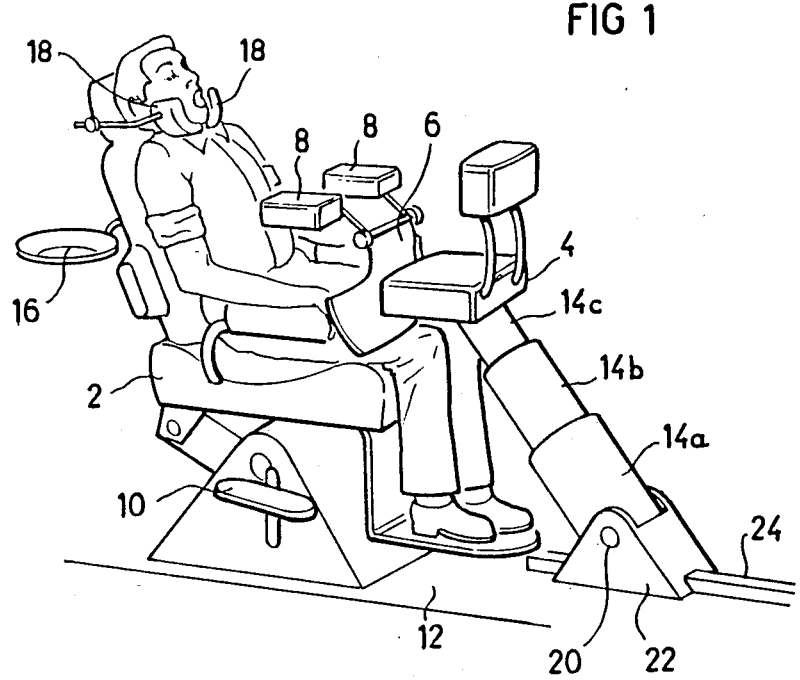
FIG. 1 illustrates one form of chair system constructed in accordance with the invention.

The chair system illustrated in the drawings is particularly useful for a dental office. It includes a chair 2 for the subject (i.e., patient) to be treated, and another chair 4 for the dentist or other operator. The subject's chair 2 may be of conventional construction for seating the subject in an upright position, but is pivotable about the vertical axis, and also about the horizontal axis to recline the subject.

Figure 2:
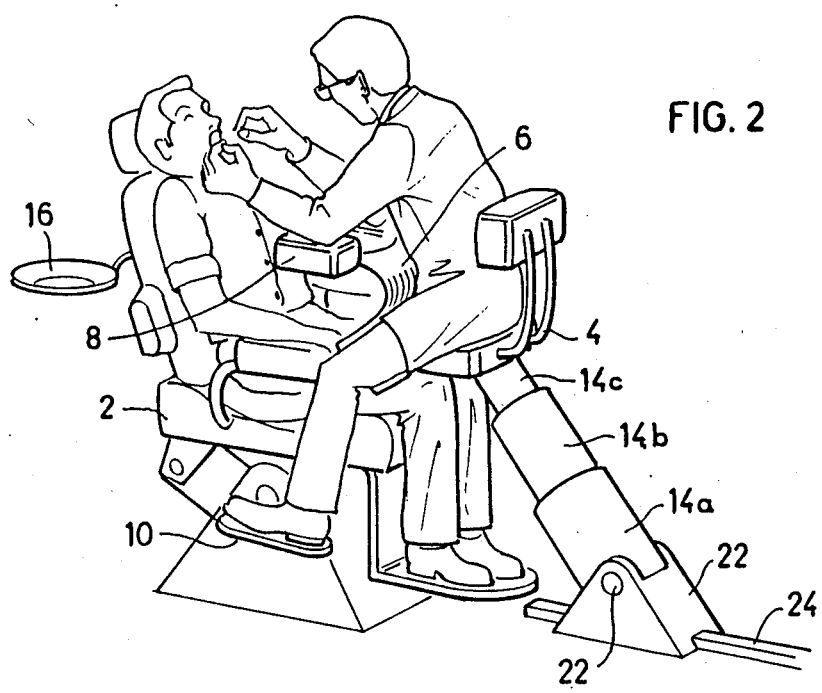
FIG. 2 illustrates the chair system of FIG. 1 with the operator's chair occupied by a dentist or other operator.

The operator's chair 4 is intended to seat the operator in an upright position facing the subject, and includes a barrier 6 separating the operator from the subject. Barrier 6 is carried by the operator's chair 4 and terminates below the head region of the subject in order to permit free access by the operator over the top of the barrier to the head region of the subject. The upper end of barrier 6 includes a pair of elbow rests for supporting the elbows of the operator when treating the head region of the subject as shown in FIG. 2. In addition, the base of the subject's chair 2 is provided with a pair of foot rests 10 raised above the floor 12, and also inclined with respect to the floor, for supporting the feet of the operator when occupying the operator's chair 4 as also shown in FIG. 2.

The operator's chair 4 is supported by an adjustable mounting 14 so as to face, but to be at a higher elevation than, the subject's chair 2. The arrangement is such, as illustrated in FIG. 2, that when the subject's chair 2 is occupied, the operator may mount the operator's chair 4 so as to face the subject, with the seat of the operator's chair substantially overlying the knees of the subject, and with the legs of the operator straddling the legs of the subject. In this position, barrier 6 separates the body of operator from that of the subject. Elbow rests 8 are used for resting the elbows of the operator in order to provide the required mechanical leverage, and foot rests 10 comfortably support the feet of the operator above the floor.

In addition, a utensils tray 16 is attached to the subject's chair 2 laterally of the chair for receiving the utensils used by the operator during the treatment. Further, the subject's chair is provided with a pair of chin rests 18 for supporting the subject's head.

The operator's chair 4 is adjustable both in the horizontal direction and in the vertical direction to locate the operator in a comfortable position with respect to the subject in the subject's chair 2. For this purpose, mounting 14 for the operator's chair 4 is made of a plurality telescoping sections 14a, 14b, 14c, driven to raise or lower the chair by a drive not shown). The lower section 14a is pivotably mounted about the horizontal axis 20 to a base 22, which base is movable along a track 24, also driven by suitable drives (not shown).

Figure 3:
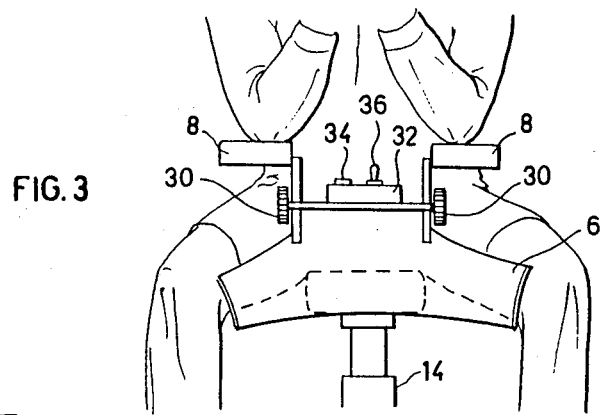
FIG. 3 is a front view illustrating the operator's chair, the barrier between the operator and subject, and the position of the operator when occupying the operator's chair during a treatment.

As shown particularly in FIG. 3, the elbow rests 8 are adjustably supported at the top of the barrier 6. A pair of knobs 30 are provided to permit convenient adjustment of the elbow rests 8. In addition, the upper end of barrier 6 is provided with a control box 32, carrying control switches 34, 36 and the like. These controls are conveniently available to the operator, when sitting in chair 4 for controlling the chair mounting 14, or other devices, while treating the subject.

It will thus be seen that the arrangement illustrated in FIGS. 1-3 provides a number of advantages over the two basic working systems described above. Thus, it permits the operator to be seated in a face-to-face relationship with the subject, thereby providing a better direct view of both the upper jaw and the lower jaw of the subject's mouth; this reduces errors of parallax and also better enables the operator to judge parallelism during tooth preparation. Further, it seats the operator at a very advantageous position such as to substantially reduce fatigue, circulatory problems, and back pain. Still further, it locates the arms of the operator at the height for maximum mechanical advantage, with the elbows of the operator resting on the elbow rests 8 so as to obtain better leverage, with the upper portions of the operator's arms in close proximity to the sides of his body, and with the forearms substantially parallel to the floor. The foot rests 10 comfortably support the feet of the operator above the floor, and the chin rests 18 comfortably support the chin of the subject while the treatment is being rendered by the operator. The chin rests also immobilize the subject's mouth to prevent movement during the treatment, which is particularly advantageous, with respect to the newer techniques using lasers and/or computers.

In the arrangement illustrated in FIGS. 1-3, track 24 which permits the operator's chair 4 and its mounting 14 to be moved towards and away from the subject, is of rectilinear configuration, aligned with the axis of the subject's chair 2 and the operator's chair 4. In such an arrangement, the dentist may pivot the subject's chair 2 about the vertical and horizontal axes in order to provide better access to, or a better view of the subject's mouth.

Figure 4:
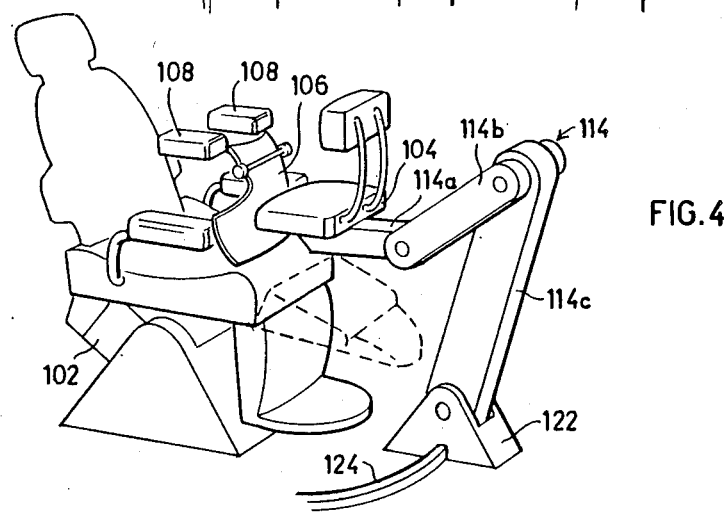
FIGS. 4 and 5 illustrate two further chair systems constructed in accordance with the invention.

FIG. 4 illustrates a variation wherein the track, therein 124, mounting the base 122 of the operator's chair 104, is of curvilinear configuration, extending along an arc intersecting the axis of the subject's chair 102 and the operator's chair 104, e.g. for about 15° on each side of this axis. This permits the operator to move the operator's chair 104 to either side of the subject's chair 102 in order to provide better access to the subject's mouth.

The arrangement illustrated in FIG. 4 also includes another type of mounting, therein designated 114, for the operator's chair 104. Thus, the mounting 114 in the FIG. 4 arrangement includes a plurality of pivotable links 114a, 114b, 114c, permitting the operator's chair to be moved toward and away from the subject's chair and also to any desired elevation with respect to the subject's chair. The adjustment of the position of the operator's chair 104 may be done manually, or may be done by the use of a suitable power drive, e.g. a piston-cylinder drive (not shown), under the control of the control buttons, corresponding to control buttons 34, 36 in FIG. 3, located at the top of the barier 106.

In all other respects, including the pivotable mounting of the subject's chair 102 about the vertical axis and also the horizontal axis (the latter being indicated by the broken-line position of the foot rests of the operator's chair 102 in FIG. 4), the chair system illustrated in FIG.

4 is the same as described above with respect to FIGS. 1–3.

Figure 5:
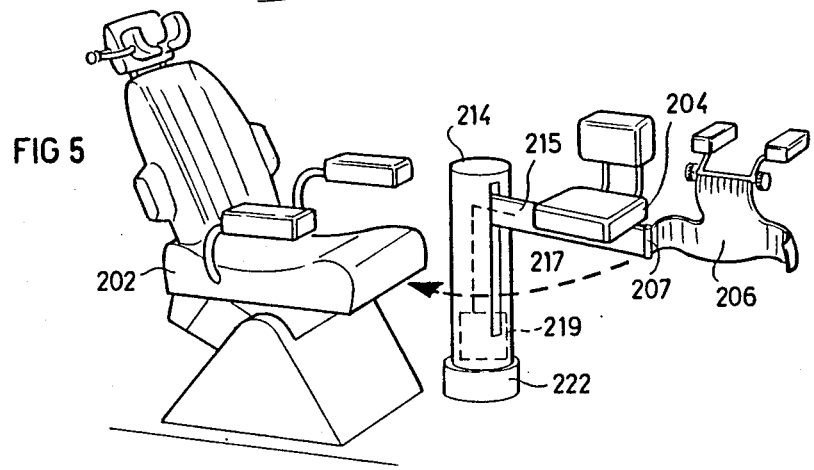

FIG. 5 illustrates another arrangement, similar to that of FIGS. 1–3, which may be used for mounting the operator's chair, therein designated 204. Thus, this mounting 214 for the operator's chair 204 includes a base 222 which is fixed to the floor. Mounting 214 is pivotable about the vertical axis of base 22, and includes a horizontal arm 215 supporting the operator's chair 204. Mounting 214 further includes a vertical slot 217 through which arm 215 projects, and a drive, schematically shown at 219, for elevating or lowering arm 215 and the operator's chair 214 supported by it.

Mounting 214 and its base 212 are both located to one side in front of the subject's chair 202. Mounting 214 is pivotable on its base 222 along the vertical axis, permitting the operator's chair 204 to be pivoted either to an operative position in alignment with the subject's chair 202, or to an inoperative position to allow the subject to seat himself in chair 202 and the operator to seat himself in chair 204. In addition, barrier 206 is pivotably mounted about vertical axis 207 to the end of the chair-supporting arm 215, allowing the operator to sit in the operator's chair 204 while the barrier 206 is in the illustrated non-operative position.

It will thus be seen that the subject first seats himself in the subject's chair 202, while the operator's chair and the barrier 206 are in their inoperative positions as illustrated in FIG. 5; the operator then seats himself in chair 204 and pivots barrier 206 about vertical axis 207 to bring the barrier in front of the operator; and then the operator pivots chair 204 about the vertical axis of base 222 to bring the chair into alignment with the subject in chair 202. The operator may then operate the drive to bring him to the most convenient elevation, as shown in FIG. 2.

It will be appreciated that the pivotable mounting 207 for the barrier 206 illustrated in FIG. 5, may also be used in the other disclosed embodiments. Also, in all the disclosed embodiments the dentist's chair and/or the patient's chair may be mounted from a wall or the ceiling, and may swivel about the vertical axis to increase the range of different positions in which the dentist can be comfortably supported with respect to the patient. Further, the dentist's chair and/or the patient's chair may be vertically adjustable to permit the dentist to conveniently work on the upper and lower teeth of the patient.

Many other variations, modifications and applications of the invention will be apparent.

What is claimed is:

1. A chair system particularly useful for a dental office or other operatory wherein the head region of a subject is to be treated by a dentist or other operator, comprising:
   a subject's chair for seating the subject in an upright position;
   an operator's chair for seating the operator in an upright position facing the subject;
   a mounting for mounting the operator's chair at a higher elevation than the subject's chair such that the legs of the operator straddle the legs of the subject when both are seated in their respective chairs;
   and a vertically-extending barrier between the operator's chair and the subject's chair terminating below the head region of the subject when seated in the subject's chair, separating the operator from the subject but permitting free access by the operator over the top of the barrier to the head region of the subject.

2. The chair system according to claim 1, wherein said barrier includes elbow rests at its upper end for supporting the elbows of the operator when treating the head region of the subject.

3. The chair system according to claim 2, wherein said elbow rests are adjustably supported at the upper end of said barrier.

4. The chair system according to claim 2, wherein said barrier and elbow rests are carried by the operator's chair.

5. The chair system according to claim 1, further including foot rests supporting the feet of the operator above the floor when the operator is seated in the operator's chair.

6. The chair system according to claim 5, wherein said foot rests are carried by the base of the subject's chair and are mounted at an incline to the floor.

7. The chair system according to claim 1, wherein said mounting of the operator's chair includes adjustable means permitting the operator's chair to be moved toward and away from the subject when the subject is seated in the subject's chair.

8. The chair system according to claim 7, wherein said mounting includes a plurality of telescoping sections permitting the operator's chair to be moved toward and away from the subject's chair.

9. The chair system according to claim 7, wherein said mounting includes a plurality of pivotable links permitting the operator's chair to be moved toward and away from the subject's chair.

10. The chair system according to claim 1, wherein said mounting is movable on a track permitting the operator's chair and its mounting to be moved with respect to the subject's chair.

11. The chair system according to claim 10, wherein said track is of rectilinear configuration and extends along the axis of the subject's chair and the operator's chair.

12. The chair system according to claim 10, wherein said track is of curvilinear configuration and extends along an arc intersecting the axis of the subject's chair and the operator's chair.

13. The chair system according to claim 1, wherein said mounting includes a base and a pivotable connection to said base permitting the operator's chair and its mounting to be pivoted about the horizontal axis to move the operator's chair closer to or away from the subject's chair.

14. The chair system according to claim 1, wherein said mounting includes a base and a pivotable connection to said base permitting the operator's chair and its mounting to be pivoted about the vertical axis to move the operator's chair either into alignment with the subject's chair when the subject is to be treated by the operator, or out of alignment with the subject's chair when the operator is to mount on or dismount from the operator's chair.

15. The chair system according to claim 1, wherein said barrier is pivotably mounted to said operator's chair permitting the barrier to be pivoted either to an operative position between the operator and the subject, or to an inoperative position laterally of the operator's chair.

16. The chair system according to claim 1, wherein said subject's chair includes a chin support for supporting the chin of the subject during the treatment.

17. The chair system according to claim 1, wherein said subject's chair includes a tray extending laterally to one side of the subject's chair for receiving utensils to be used by the operator during the treatment.

18. The chair system according to claim 1, wherein said subject's chair is pivotable about the vertical axis.

19. The chair system according to claim 1, wherein said subject's chair is reclinable about the horizontal axis.

20. A chair system particularly useful for a dental office or other operatory wherein the head region of a subject is to be treated by a dentist or other operator, comprising:

a subject's chair for seating the subject in an upright position;

an operator's chair for seating the operator in an upright position facing the subject;

a mounting for mounting the operator's chair at a higher elevation than the subject's chair such that the legs of the operator straddle the legs of the subject when both are seated in their respective chairs;

a vertically-extending barrier between the operator's chair and the subject's chair terminating below the head region of the subject when seated in the subject's chair, separating the operator from the subject but permitting free access by the operator over the top of the barrier to the head region of the subject;

said barrier including elbow rests at its upper end for supporting the elbows of the operator when treating the head region of the subject, and foot rests supporting the feet of the operator above the floor when the operator is seated in the operator's chair, said foot rests being carried by the base of the subject's chair and being mounted at an incline to the floor.

* * * * *